(12) United States Patent
Karam et al.

(10) Patent No.: US 7,572,222 B2
(45) Date of Patent: Aug. 11, 2009

(54) DEVICE FOR ANALYZING THE PHYSICOCHEMICAL PROPERTIES OF A CUTANEOUS SURFACE

(75) Inventors: Jean-Michel Karam, Grenoble (FR); Eric Viviant, Meylan (FR)

(73) Assignees: MEMSCAP, Crolles (FR); Laboratoires La Licorne, Le Plessis Robinson (FR)

( * ) Notice: Subject to any disclaimer, the term of this patent is extended or adjusted under 35 U.S.C. 154(b) by 282 days.

(21) Appl. No.: 10/826,103

(22) Filed: Apr. 16, 2004

(65) Prior Publication Data

US 2004/0199058 A1    Oct. 7, 2004

Related U.S. Application Data

(63) Continuation of application No. PCT/FR02/02077, filed on Jun. 16, 2002.

(30) Foreign Application Priority Data

Oct. 29, 2001    (FR) .................................. 01 13989

(51) Int. Cl.
*A61B 5/00* (2006.01)
(52) U.S. Cl. ...................... 600/306; 600/549
(58) Field of Classification Search ............... 600/306
See application file for complete search history.

(56) References Cited

U.S. PATENT DOCUMENTS

| 4,733,383 | A | * | 3/1988 | Waterbury | 368/10 |
|---|---|---|---|---|---|
| 4,813,412 | A | * | 3/1989 | Yamazaki et al. | 606/46 |
| 5,588,440 | A | * | 12/1996 | Cowie | 600/547 |
| 5,938,593 | A | * | 8/1999 | Ouellette | 600/300 |
| 6,251,070 | B1 | * | 6/2001 | Khazaka | 600/306 |
| 6,370,426 | B1 | * | 4/2002 | Campbell et al. | 600/547 |
| 6,433,244 | B1 | * | 8/2002 | Roe et al. | 604/361 |
| 6,676,611 | B1 | * | 1/2004 | Bromba | 600/587 |
| 6,712,771 | B2 | * | 3/2004 | Haddock et al. | 600/549 |
| 6,944,491 | B2 | * | 9/2005 | Leveque | 600/407 |
| 2003/0064356 | A1 | * | 4/2003 | Rubinstenn et al. | 434/377 |

FOREIGN PATENT DOCUMENTS

| EP | 0 799 599 A1 | 10/1997 |
|---|---|---|
| FR | 2 603 183 A1 | 3/1988 |
| JP | 10-234676 A1 | 9/1998 |
| WO | WO 01/41417 A1 | 6/2001 |

\* cited by examiner

*Primary Examiner*—Robert L. Nasser, Jr.
(74) *Attorney, Agent, or Firm*—Burr & Brown

(57) ABSTRACT

The invention relates to a device for analysing the physicochemical properties of a cutaneous surface comprising: a group of sensors which are assembled at an acquisition zone (4), opposite which the cutaneous surface to be analysed is positioned; and a processing unit (1) which is interfaced with the group of sensors, said unit being equipped with analysis means that can be used to determine certain physico-chemical properties of the cutaneous surface to be analysed using signals produced by said group of sensors.

21 Claims, 1 Drawing Sheet

DEVICE FOR ANALYZING THE PHYSICOCHEMICAL PROPERTIES OF A CUTANEOUS SURFACE

CROSS REFERENCE TO RELATED APPLICATIONS

This application is a continuation of International Application No. PCT/FR02/02077 having an international filing date of Jun. 16, 2002, which designated the United States, the entirety of which is incorporated herein by reference.

This application claims the benefit of French Application 01.13989, filed Oct. 29, 2001, the entirety of which is incorporated herein by reference.

FIELD OF THE INVENTION

The invention concerns the field of cosmetology and dermatology. It relates more particularly to a device for analyzing various physicochemical properties of a cutaneous surface, so as to make it possible to diagnose a possible treatment, and optionally to indicate which treatment products would be most appropriate.

PRIOR ART

As is known, the skin acts as a barrier between the body and the external medium. It fulfills a role of physically protecting the body, and many exchanges between the body and the external medium take place within it.

Such exposure to the external medium may cause degradation of its mechanical strength capacities, as well as its visual appearance. Many factors, in particular atmospheric conditions and also pollution phenomena, can cause modification of the structure of the skin and degradation of these essential functions.

For instance, excessive exposure to ultraviolet radiation from the sun, or to an atmosphere in which the relative humidity is too low, can cause modification of the metabolism of the skin cells, for example accelerated ageing.

Skin drying phenomena are then observed, or the appearance of creases or wrinkles. Until now, the diagnosis of a treatment intended to reduce the extent of these creases has been carried out by visual examination of the cutaneous regions to be treated. Precise quantification of the extent of these creases cannot be carried out rapidly and in a generalized way.

The existence of sophisticated machines or devices that include microscopic imaging instruments for visualizing the shape and the various dimensions of a furrow of creases is known. Such machines are extremely complex and only a limited number of them exist, which means that they cannot be used widely enough.

Furthermore, the treatment of cutaneous dryness or too high a level of lipids is generally diagnosed by visual observation, or examination of the skin by touch. The limitations of such examination, which does not allow a plurality of symptoms to be picked up simultaneously, are evident. It is moreover known that various factors, such as a low skin moisture content or a high lipid content, may interfere with this and lead to diagnosis errors. A treatment which is not appropriate, however, may tend to exaggerate the problems for which it is trying to compensate.

The present invention is intended to facilitate diagnosis of the cutaneous treatment by an objective and rigorous analysis of the physicochemical properties of the skin.

Documents FR 2 603 183 and JP 10 234676 describe devices for measuring the properties of the skin, which use specific sensors. Such devices have one or more different probes which are connected an electronic processing unit. The signals generated by these various probes are analyzed in relation to predetermined thresholds, in order to indicate the position of the measured values with respect to the predetermined thresholds. It can be seen that the measurements carried out by this type of device are not really satisfactory, since it does not take into account the influences of various skin parameters on one another, and this leads to risks of diagnosis errors. When wishing to measure a plurality of parameters relating to a localized region of the skin, moreover, the use of separate probes means that it is necessary to position the various probes successively at the same position on the skin, with risks of errors and a long operating time.

It is therefore an object of the present invention to allow precise and homogeneous analysis of a plurality of skin parameters, on the same localized region of the skin.

SUMMARY OF THE INVENTION

The invention relates to a device for analyzing the physicochemical properties of a cutaneous surface, which has a set of sensors grouped and located in an acquisition region, in front of which the cutaneous surface to be analyzed is intended to be placed.

This device also comprises a processing unit interfaced with the set of sensors. This unit is equipped with analysis means for determining certain physicochemical properties of the cutaneous surface to be analyzed, on the basis of the signals produced by the set of sensors.

In other words, the device according to the invention allows the user to simultaneously determine a variety of different types of information, relating to a particular region of his or her cutaneous surface. This information as a whole can then be decoded so as to determine each of the physicochemical properties of the cutaneous surface which is of interest with a view to the future treatment.

The term "cutaneous surface" is of course intended to mean all of the cutaneous envelope, including the regions with hair, and in particular the scalp.

Since the sensors are grouped in a limited region, this makes it possible to obtain results representing the same region for all the parameters being analyzed. This arrangement also makes it possible to acquire the set of parameters simultaneously, in a very short time.

In practice, the set of sensors preferably comprises at least:
a pH sensor;
a cutaneous print sensor, capable of measuring the topography of the cutaneous surface to be analyzed;
a skin moisture sensor.

The skin pH measurement makes it possible to distinguish between a high pH, of the order of 5.5, and a more acid pH of close to 5.

The skin moisture sensor makes it possible to measure more precisely the parameter generally referred to as "transepidermal water loss", abbreviated to TEWL. This parameter corresponds to the evaluation of a phenomenon that is independent of transpiration, involving the evaporation of water from the underlying layers of the epidermis. This measurement makes it possible, for example, to monitor the hydro lipid film which carries out the role of a skin barrier function, and to define the scale of cutaneous dryness of the skin.

The cutaneous skin sensor makes it possible to take a measurement of the various irregularities of the surface of the skin. This measurement may be carried out according to various principles, such as a capacitive, piezoresistive, piezoelectric, optical or electromagnetic measurement. Determining the topography of the region to be analyzed makes it possible to measure the regularity of the skin, the number of creases, their length, their area and their average depth. The total area of the creases may be determined by calculating the area occupied by the medium and deep creases corresponding, respectively, to creases whose depth lies between 150 and 200 micrometers and more than 200 micrometers.

It is also possible to determine the extent of the major furrows, so as to take account of the length of the deepest creases. Determining the value of the major creases makes it possible to measure the variation of these creases over time.

The skin roughness measurement is also an important parameter, because it gives access overall to the notion of planarity of the skin by characterizing it with an average amplitude value, which is the sum of the various relief attributes in comparison with a plane surface. Measuring this roughness parameter, and its variation over time, makes it possible to investigate the smoothing of the skin due to a particular treatment.

In a more sophisticated form of the invention, the analysis device may comprise additional sensors, such as a temperature and/or ambient humidity sensor, a lipid level sensor and a sensor for elastic deformation of the cutaneous surface to be analyzed.

Measuring the temperature or the ambient humidity makes it possible to correct some particular measurements, especially that of the moisture content of the skin, i.e. the "transepidermal water loss". It also makes it possible to validate a diagnosis with respect to the atmospheric conditions.

The lipid level sensor makes it possible to determine the status of the cutaneous lipids, in particular for dry skins. This measurement makes it possible to distinguish the phenomenon of cutaneous dryness from the phenomenon of excessive sebum production.

The sensor for elastic deformation of the cutaneous surface to be analyzed makes it possible to measure the tautness and the elasticity of the skin. This measurement is, in particular, a function of temperature. This deformation sensor operates on the principle of applying a reduced pressure to a skin region for a constant time. A plurality of successive suctions may be carried out so as to measure the penetration depth of the skin in the probe. More precisely, this measurement may be carried out by means of optical sensors or ones based on strain gauges, for example.

Analyzing the various measurements which are obtained makes it possible to distinguish between instantaneous deformations, corresponding to an elasticity phenomenon, and delayed deformations similar to a viscosity phenomenon.

The various sensors installed on the acquisition region are preferably made by technologies of the MEMS type, standing for "Micro-Electromechanical System". These sensors are therefore produced according to technologies which use semiconductor, insulating or metallic materials, and chemical machining methods that are employed in the field of microelectronics. Using sensors of the MEMS type makes it possible to concentrate the set of sensors on a particularly small region, which is fitted on a single probe. This makes it possible to obtain results representing a localized region that is homogeneous in respect of its characteristics. The prior art solutions which employ a plurality of different probes for carrying out a series of measurements, conversely, are much less precise since they make the operating mode more complicated. They furthermore use bulkier and therefore more expensive equipment.

The analysis device may be embodied in several geometries.

In a first embodiment, for instance, the acquisition region may be arranged on a fixed base intended to come in contact with the cutaneous surface. This hence involves a station onto which the user will apply a particular region of his or her cutaneous surface, typically on the hand or forearm. In another embodiment, the acquisition region may be arranged on a mobile component, which is electrically connected to the processing unit and which can be moved in front of the cutaneous region to be analyzed. In this case, the mobile component is removable and can be applied to any part of the body.

In a preferred form, the mobile component forming the probe is connected to the processing unit by a wireless connection. In other words, the signals generated by the sensors are transmitted to the processing unit, optionally with an initial shaping operation, by a connection of the radiowave type. This arrangement makes the handling operations more flexible, since it is thus possible to move the probe in space, over different cutaneous regions of the same patient or inside the room where the device is arranged, while being limited only by range considerations of the wireless connection. In practice, for example, the connection may function according to the technology known by the name "Bluetooth". The frequency band dedicated to industrial applications, also known by the abbreviation ISM Band for "Industrial Scientific Medical Band", could be used in particular.

When a wireless connection is used, it is also possible to combine a plurality of different probes with a single treatment unit. In this way, analyses may be carried out simultaneously on a plurality of subjects, so long as the wireless connection protocol makes it possible to identify the different probes, and so long as the processing means can carry out calculations in parallel.

In practice, the processing unit may preferably be connected to a display terminal, or to a printing or transmission system for either visualizing or processing the results of the analysis.

The processing unit can preferably classify the analyzed cutaneous surface in a predetermined category, as a function of the physicochemical properties which are determined. In other words, the device according to the invention allows precise analysis of the skin as a whole, which makes it possible to determine a skin typology by comparison with statistical or analytical data prerecorded in the processing unit.

The processing unit is preferably associated with a database of treatment products, making it possible to inform the user about the product most appropriate for the condition of his or her skin, this product being selected from a range prerecorded in the database.

In certain applications, provision may be made to connect a plurality of analysis devices through a computer network, with additional advantages. For instance, the processing units may in particular be connected via the Internet, or alternatively via other connection modes operating on private networks or the like. In this way, a computer fulfilling the role of a server may be installed on this analysis-device network. This server may record the different data produced in the various processing units which are connected to it, so as to formulate miscellaneous statistics about the various analyses which have been carried out. This networking also makes it possible for a given subject to gain access to the results of previous analyses, carried out on devices which are at another location or, more generally, which are different. A history and analysis of the variation in the properties of a subject's skin may thus be established, in particular making it possible to evaluate the effect of a treatment prescribed in the past, by using a device according to the invention. Furthermore, this networking also makes it possible to update the various processing units in respect of the analysis criteria, and the products which could be prescribed.

In a particular embodiment, the device may also have means that can sterilize the acquisition region after each use. These means may be either manual, with the probe being soaked in an appropriate solution. It may also be possible to wipe the region with an appropriate cleaning article. An automatic system may also be provided in order to remove from the acquisition region any impurity intended to come in contact with the next user's skin.

BRIEF DESCRIPTION OF THE DRAWINGS

The way in which the invention may be embodied, and the advantages which are provided thereby, will become readily apparent from the description of the embodiment which follows with reference to the appended figures, in which.

EMBODIMENT OF THE INVENTION

As mentioned above, the invention relates to a device for analyzing the physicochemical properties of a cutaneous surface.

Figure 1:
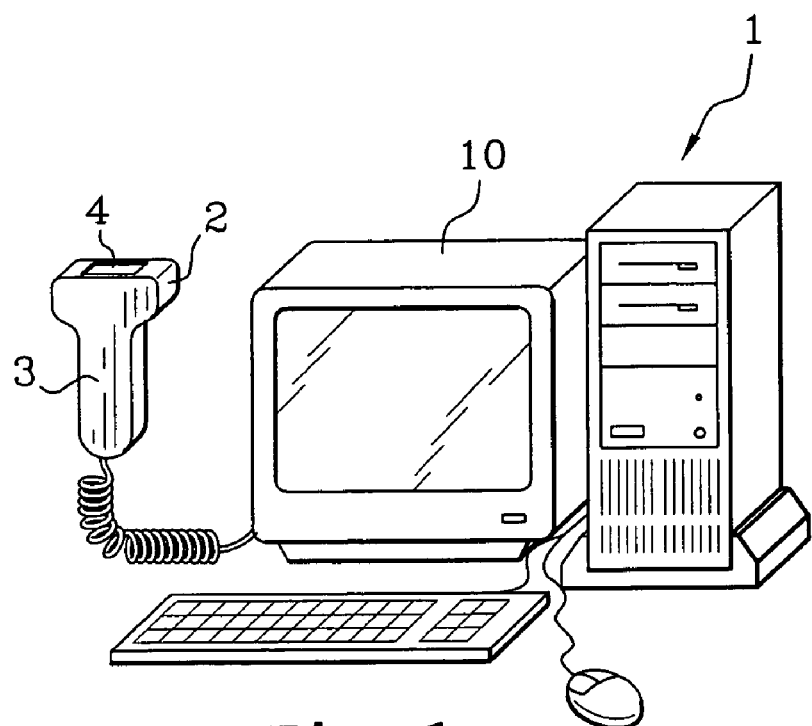
FIG. 1 is an overall view of the device according to the invention, including a processing unit and a removable acquisition region.

Such a device may, as illustrated in FIG. 1, be in the form of a microcomputer (1) with which a mobile component (2) or probe is associated, the latter having a handle (3) and an acquisition region (4) arranged on the upper part of this mobile component (2).

Figure 2:
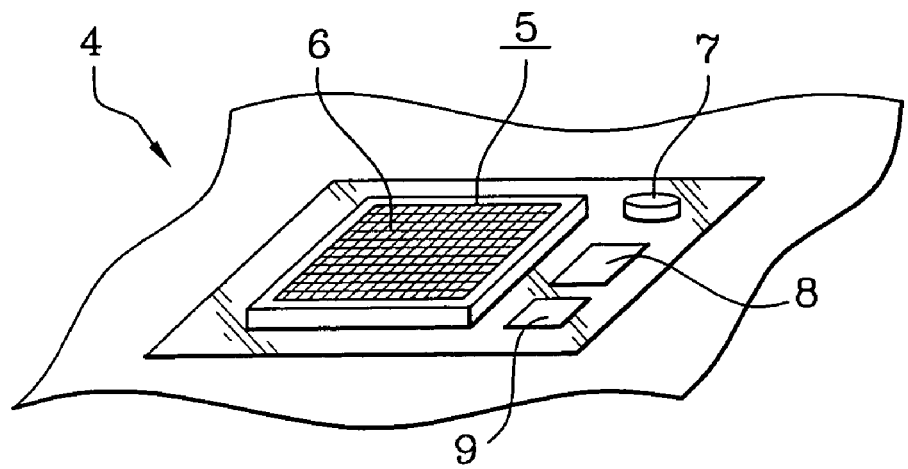
FIG. 2 is a summary perspective view of the acquisition region.

More precisely, and as illustrated in FIG. 2, this acquisition region has a surface area of a few square centimeters and, under a protective surface, it groups together the various sensors necessary for analyzing the physicochemical characteristics of the cutaneous surface on which the mobile component is placed.

More precisely shown is the cutaneous print sensor (5), which may for example correspond to the sensor type marketed by ATMEL under the brand name FINGER CHIP®. This sensor, operating for example on the principle of a capacitive measurement, delivers a two-dimensional image of the cutaneous region. By processing this image, an evaluation of the depth of the observed furrows may be made. This processing allows a depth measurement of the furrows of the skin with a resolution of the order of about ten microns.

It is nevertheless possible to use other sensors, operating on different physical principles such as the phenomena of piezoelectricity, piezoresistivity, or by using electromagnetic or optical phenomena.

The acquisition region (4) illustrated in FIG. 1 also shows an ambient humidity sensor (7), which may correspond to the type marketed by HUMIREL under the references HS 1100 and HS 1101, or the like. This type of sensor operates by measuring the variation in the capacitance of an elementary cell as a function of the ambient relative humidity. The invention is, of course, not limited to using just this type of sensor, and it covers variants which operate on the same principle and are embodied using MEMS technologies.

The acquisition region (4) illustrated in FIG. 2 also shows a pH sensor (8) made using MEMS technologies, which may for example be produced on the basis of IFSET components (for "ION SELECTIVE FIELD EFFECT TRANSISTOR").

Furthermore, the acquisition region (4) illustrated in FIG. 2 also has a temperature sensor (9), for taking information about the skin temperature into account when formulating the various analysis of the physicochemical properties of the skin.

If the various sensors operate on the basis of physical principles liable to create interference, appropriate positions will be selected, or screens or other similar means, to limit unsuitable interactions between the various sensors.

In some variants, the acquisition region may also include a lipid level sensor, operating on the principle of measuring the optical transmission/reflection properties of a film. This film, optionally containing cavities, becomes filled with sebum by contact with the skin. Its optical properties are modified by this, according to the amount of sebum absorbed. An optical MEMS sensor is associated with this film.

The probe also includes a sensor for the skin moisture, or more precisely the "transepidermal water loss" or TEWL. This sensor, produced using MEMS technologies, contains a polymeric film which condenses the water vapor evaporating from the cutaneous layer. The sensor reacts according to the variations in the electrical properties of this film, as a function of the amount of water vapor condensed.

Other sensors may be integrated in the probe, according to the intended applications. For instance, an optical MEMS sensor may be used which is intended to determine the extent of hair follicularization on the scalp.

The set of signals generated by the various sensors is processed by shaping circuits, allowing the various signals to be acquired by an acquisition card present in the computer (1), in the case of a wired connection between the probe (2) and the computer (1). In the case of a wireless connection between the processing unit, the signals are shaped with a view to being transmitted from the probe toward the processing unit. As mentioned above, a plurality of probes of the same type may be associated with a single processing unit.

Analysis of the different signals coming from the various sensors is then carried out in the central processing unit of the computer (1). This analysis makes it possible to classify the analyzed skin among various predetermined categories, examples of which may include dry skins, greasy skins, normal skins, mixed skins, reactive skins, etc.

When the device is used by a dermatologist, or more generally a physician, it allows him or her to identify possible pathologies or insufficiencies that may be remedied by an appropriate treatment which the medical practitioner can then recommend.

However, the device may also be interfaced with a database of cosmetic products, the prescription of which does not require intervention by a physician. In this case, the product or products most appropriate for treating the symptoms detected by the analysis may be displayed directly on the screen (10) for the user.

Of course, the device may also be used outside the scope of a surgery. This being the case, for example, it may, in particular, be used in a perfume shop or in a drugstore, or in general at any premises where dermatological and/or cosmetic products are sold. The device may then adopt a different configuration, in which the user is allowed access only to the acquisition region and the display screen, with everything being placed in a base or fixture in order to make it into an analysis station.

The description given above shows that the device according to the invention has many advantages, in particular that of allowing rigorous, targeted, simultaneous and rapid analysis of a plurality of physicochemical properties of the same skin sample, with a view to determining possible insufficiencies or pathologies. It also makes it possible to carry out a plurality of different analyses in parallel, by using devices that have a plurality of probes. It may advantageously be associated with a database of treatment products, so as to facilitate the user's selection. In a network configuration, these devices make it possible to gain access to statistics, and histories of analyses, irrespective of where the consultations took place.

The invention claimed is:

1. A device for analyzing the physicochemical properties of a cutaneous surface, the device comprising:
    a handheld mobile component;
    an acquisition region located along a single side of said handheld mobile component, the acquisition region being sized to cover a cutaneous surface to be analyzed;
    at least three sensors grouped and located within said handheld mobile component and directed toward the acquisition region, the sensors being a temperature sensor for measuring the temperature of the cutaneous surface, a skin TEWL sensor for measuring the transepidermal water loss, and an ambient humidity sensor; and
    a processing unit interfaced with the set of sensors, said unit being equipped with analysis means for determining certain physicochemical properties of the cutaneous surface to be analyzed, on the basis of signals produced by said sensors.

2. The device as claimed in claim 1 further comprising
    a pH sensor, and
    a cutaneous print sensor, capable of measuring the topography of the cutaneous surface to be analyzed.

3. The device as claimed in claim 1 further comprising
    a lipid level sensor and
    a sensor for elastic deformation of the cutaneous surface to be analyzed.

4. The device as claimed in claim 1, wherein at least one of said sensors is made from micro-electromechanical systems (MEMS).

5. The device as claimed in claim 1, wherein the acquisition region is electrically connected to the processing unit and can be moved in front of the cutaneous surface to be analyzed.

6. The device as claimed in claim 1, wherein the mobile component is connected to the processing unit by a wireless connection.

7. The device as claimed in claim 6, wherein the wireless connection is a radio frequency connection.

8. The device as claimed in claim 1, wherein the processing unit is connected to a display terminal.

9. The device as claimed in claim 8 further comprising a plurality of handheld mobile components, each including an acquisition region, which are connected to the processing unit.

10. The device as claimed in claim 1, wherein the processing unit classifies the cutaneous surface to be analyzed in a predetermined category, as a function of the physicochemical properties which are determined.

11. The device as claimed in claim 1, wherein the processing unit is associated with a database of treatment products.

12. The device as claimed in claim 1 further comprising a pH sensor.

13. The device as claimed in claim 1 further comprising a cutaneous print sensor capable of measuring the topography of the cutaneous surface to be analyzed.

14. The device as claimed in claim 1 further comprising a lipid level sensor.

15. The device as claimed in claim 1 further comprising a sensor for elastic deformation of the cutaneous surface to be analyzed.

16. The device as claimed in claim 1 further comprising a pH sensor and a lipid sensor.

17. The device as claimed in claim 1 further comprising a pH sensor and a sensor for elastic deformation of the cutaneous surface to be analyzed.

18. The device as claimed in claim 1 further comprising a cutaneous print sensor capable of measuring the topography of the cutaneous surface to be analyzed and a lipid level sensor.

19. The device as claimed in claim 1 further comprising a cutaneous print sensor capable of measuring the topography of the cutaneous surface to be analyzed and a sensor for elastic deformation of the cutaneous surface to be analyzed.

20. The device as claimed in claim 1 further comprising a pH sensor, a cutaneous print sensor capable of measuring the topography of the cutaneous surface to be analyzed, and a lipid level sensor.

21. The device as claimed in claim 1, wherein the TEWL sensor is a micromechanical system (MEMS) sensor comprising a polymeric film that condenses the water vapor evaporating from the cutaneous layer, the TEWL sensor being able to react according to the variation in the electrical properties of said film, as a function of the amount of water vapor condensed.

* * * * *